United States Patent
Foxman

(10) Patent No.: US 10,251,634 B2
(45) Date of Patent: Apr. 9, 2019

(54) SCLERAL DEPRESSOR

(71) Applicant: Brett Foxman, Margate, NJ (US)

(72) Inventor: Brett Foxman, Margate, NJ (US)

( * ) Notice: Subject to any disclaimer, the term of this patent is extended or adjusted under 35 U.S.C. 154(b) by 436 days.

(21) Appl. No.: 15/047,724

(22) Filed: Feb. 19, 2016

(65) Prior Publication Data
US 2017/0238919 A1 Aug. 24, 2017

(51) Int. Cl.
*A61B 17/02* (2006.01)
*A61B 90/00* (2016.01)

(52) U.S. Cl.
CPC .. *A61B 17/0231* (2013.01); *A61B 2090/0817* (2016.02)

(58) Field of Classification Search
CPC .................................. A61B 17/0231
USPC .................. 600/235, 236, 245, 239, 240
See application file for complete search history.

(56) References Cited

U.S. PATENT DOCUMENTS

| 2,224,575 A | 12/1940 | Montalvo-Guenard |
| 4,453,546 A | 6/1984 | Katz et al. |
| 5,409,457 A | 4/1995 | Del Cerro et al. |
| 7,419,493 B2 | 9/2008 | Olsen et al. |
| 8,083,751 B2 | 12/2011 | Olsen et al. |
| 8,235,893 B2 | 8/2012 | Josephberg et al. |
| 8,915,848 B1 * | 12/2014 | Rixen ............ A61B 1/32 600/235 |
| 2009/0115643 A1 | 5/2009 | Goffman |

OTHER PUBLICATIONS

Morizane Scleral Depressor.

* cited by examiner

*Primary Examiner* — Anu Ramana
(74) *Attorney, Agent, or Firm* — Norman E. Lehrer

(57) ABSTRACT

A scleral depressor includes an elongated handle defining a first axis. An extension member has one end attached to the proximal end of the handle and includes a blade at the remote end thereof. The extension member defines a second axis and extends from the handle at approximately 90° thereby defining a plane. A bulbous or cylindrically shaped blade located at the remote end of the extension member has its rounded surface extending out of the plane. By properly manipulating the handle, such as by rotating the same, the rounded surface of the blade is used to depress the sclera.

4 Claims, 1 Drawing Sheet

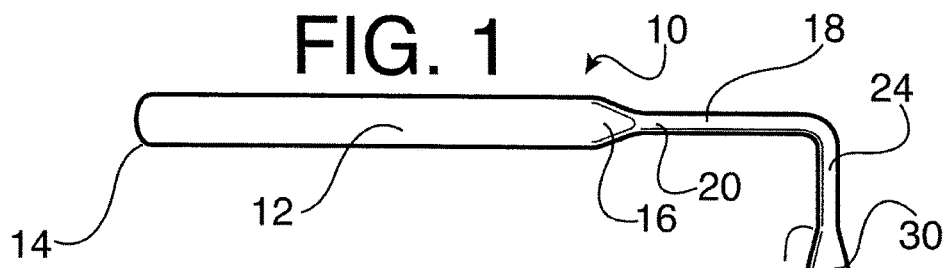
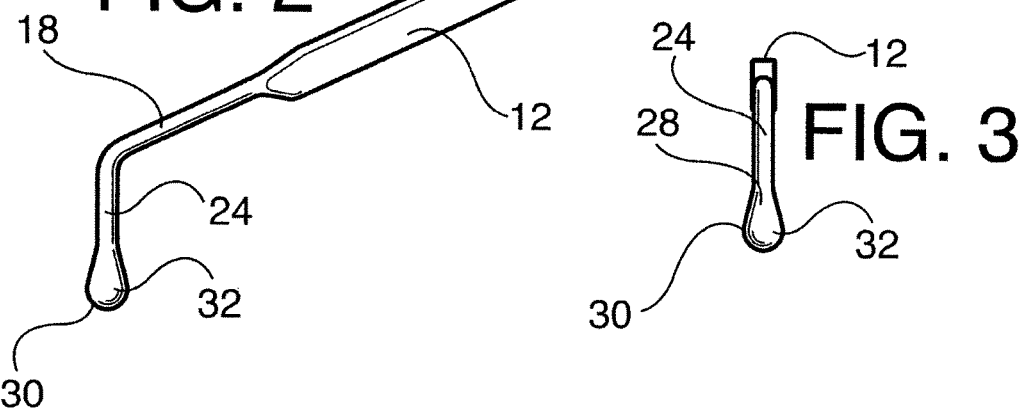
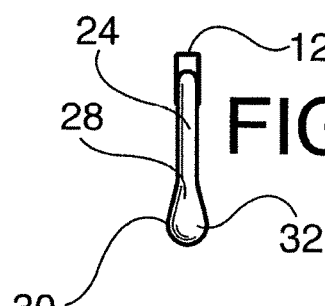
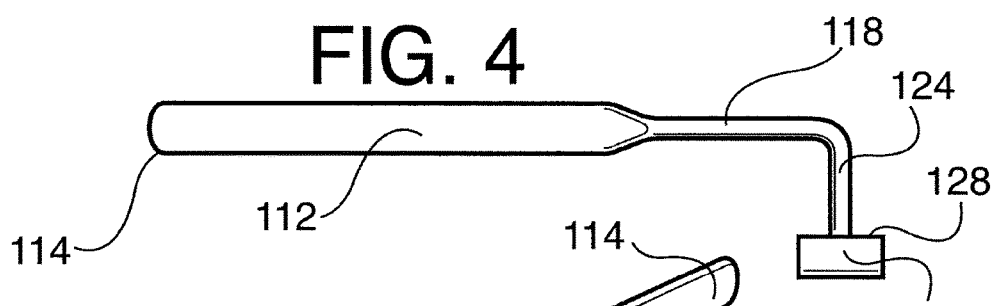
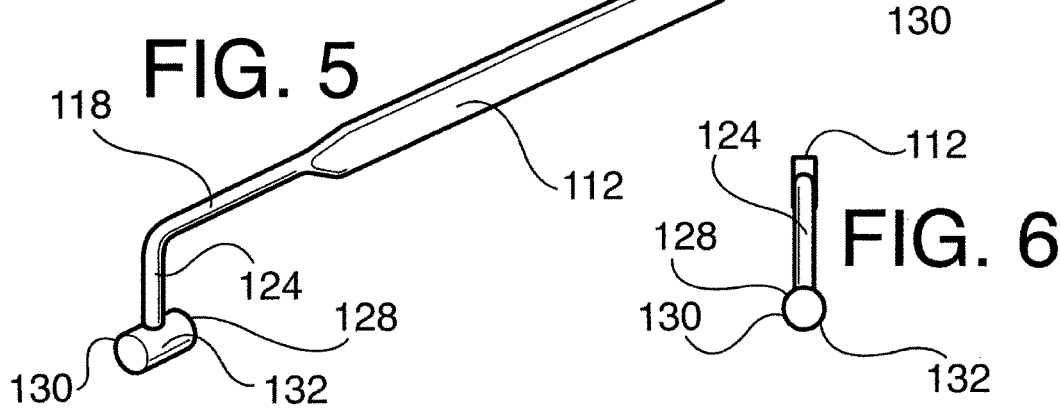
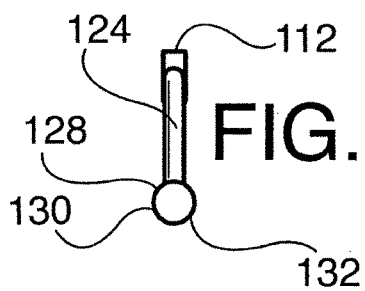

SCLERAL DEPRESSOR

FIELD OF THE INVENTION

The present invention is directed toward an ophthalmic surgical and examination instrument used during surgery or during an eye examination for depressing the sclera. More particularly, the invention relates to a scleral depressor that provides improved manipulation and does not interfere with the examining physician's field of view.

BACKGROUND OF THE INVENTION

As is well known in the art, scleral depressors are used to facilitate examination of the fundus or interior surface of the eye including the retina. During such an examination, and particularly during the study of areas of the retina, it is sometimes necessary to control the position of the eye.

During vitrectomy surgery, instruments are placed through the sclera or white wall of the eye, into the vitreous cavity to repair or correct problems inside the eye. Complete surgical dissection of the peripheral vitreous and retina is not possible without deliberate depression of the sclera. Under most situations, the surgeon's hands are occupied with the surgical instruments. Accordingly, an assistant is required to perform "scleral depression." Several sclera depressors have been designed for this purpose.

Substantially all known prior art sclera depressors include a handle and a blade or depressing element that is attached to the handle and which extends therefrom. The blade is arranged to be either straight or at an offset angle from the handle to facilitate manipulation of the blade.

One known example of such a scleral depressor is available from Inami Ophthalmic Instruments under the name Morizane. The blade of the Morizane scleral depressor is in the form of a relatively flat triangle that faces in the same direction as the direction of the axis of the elongated handle. The depressor is designed to allegedly control the rotation of the eyeball along with the depression of the same.

Scleral depressors used during surgery typically have a blade depressing element in the form of a cylinder or that has a bulbous structure. The classical and optimal means to provide depression during surgery involves inserting the scleral depressor parallel to the axis of the eye and depressing the sclera in toward the center of the eye, perpendicular to the wall of the eye.

Typically, the patient is lying in a supine position with the surgeon at the top of the head and the assistant at the side, oriented 90° from the surgeon. The face and body of the patient are covered by sterile cloths with the operative eye being the only exposed body part.

Using the current straight scleral depressors that are available, the assistant, who is typically on the temporal or lateral side of the eye, has several obstacles to adequate scleral depression. For example, depression on the nasal side of the eye is difficult to access as it's on the opposite side as the assistant. His or her hand has to reach all the way around the eye to access this region. The superior side of eye is also difficult to access due to the assistant's hand interfering with the surgeon's hands and instruments and the inferior side of the eye is slightly limited to depression by the cheekbone. Even further, the handle and shaft of the depressor frequently hit the optical system for viewing inside the eye which are either hanging from the microscope above the eye (with the lowermost portion a few millimeters above the eye) or are sitting on the surface of the eye.

There is, therefore, a need for a scleral depressor that allows an assistant to apply a depression force to the sclera at almost any location and in almost any direction without interfering with the surgeon or any of the surgical instruments.

SUMMARY OF THE INVENTION

The present invention is designed to overcome the deficiencies of the prior art discussed above. It is an object of the present invention to provide a scleral depressor that, when in use during surgery, can depress the sclera at substantially any desired location while avoiding other instruments.

It is another object of the present invention to provide a scleral depressor that, when in use during surgery, does not interfere with a surgeon's field of view.

It is a still further object of the present invention to provide a scleral depressor that, when in use during surgery, can be easily slid along the surface of the eye to a desired position without interfering with other instruments or with a surgeon's field of view.

In accordance with the illustrative embodiments demonstrating features and advantages of the present invention, there is provided a scleral depressor particularly suited for use during surgery that includes an elongated handle defining a first axis. An extension member has one end attached to the proximal end of the handle and includes a blade at the remote end thereof. The extension member defines a second axis and extends from the handle at approximately 90° thereby defining a plane. A bulbous or cylindrically shaped blade located at the remote end of the extension member has its rounded surface extending out of the plane. By properly manipulating the handle, the rounded surface of the blade is used to depress the sclera.

Other objects, features, and advantages of the invention will be readily apparent from the following detailed description of the preferred embodiment thereof taken in conjunction with the drawings.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

FIG. 1 is a side elevational view of first embodiment of a scleral depressor showing my invention;

FIG. 2 is a perspective view of the first embodiment of the invention shown in FIG. 1;

FIG. 3 is a front elevational view of the first embodiment;

FIG. 4 is a side elevational view showing a second embodiment of my invention;

FIG. 5 is a perspective view of the second embodiment of the invention shown in FIG. 4, and FIG. 6 is a front elevational view of the second embodiment.

DETAILED DESCRIPTION OF THE PREFERRED EMBODIMENTS

With reference now to the drawings in detail wherein like reference numerals have been used throughout the various figures to designate like elements, there is shown in FIGS. 1, 2 and 3 a first embodiment of a scleral depressor constructed in accordance with the principles of the present invention and designated generally as 10.

The scleral depressor 10 is comprised essentially of an elongated handle 12 which defines a first axis. The handle 12 includes a distal end 14 and a proximal end 16. An extension 18 of the handle 12 has its first end 20 attached to the proximal end 16 of the handle and includes a second remote end 22.

As shown in FIG. 1, the extension member 18 is bent so that the latter portion or member 24 thereof defines an axis which is between approximately 90° to 120° from the axis of the handle 12. In the preferred embodiment of the invention, the second axis is approximately 90° from the first axis.

The axes of the handle 12 and of the portion 24 of the extension member 18 essentially define a plane which, as viewed in FIG. 1, is the plane of the paper.

A blade 28 is carried by the remote end 22 of the extension member 24 and includes rounded surfaces 30 and 32 on the sides thereof. As shown best in FIG. 3, the rounded surface 30 extends in a first direction out of the plane approximately 90° to the plane and beyond the side of the extension member 24. The second rounded surface 32 extends in a second direction substantially opposite to the first direction and out of the plane and, again, beyond the side of the extension member 24 as viewed in FIG. 3. The blade 28 in the first embodiment is essentially bulbous shaped but other shapes are possible. In any case and as can be seen in FIG. 3, the blade is wider than the extension member 24.

The second embodiment of the invention as shown in FIGS. 4, 5 and 6 is similar in most respects to the first embodiment shown in FIGS. 1, 2 and 3 and described above. Accordingly, many of the parts thereof will not be re-described and are referenced by the same reference numerals as above but preceded by a 1.

The only significant difference between the two embodiments is in the blade. In lieu of the bulbous blade 28, the second embodiment utilizes a cylindrically shaped blade 128. As shown most clearly in FIG. 6, the outer surface of the cylinder 128 provides the rounded surfaces 130 and 132 that extend in opposite directions out of the plane defined by the handle 112 and the lower portion 124 of the extension member 118. As with the first embodiment, and as best seen in FIG. 6, the diameter of the cylindrically shaped blade from left to right is wider than the extension member 118.

The improved scleral depressor 10 or 110 of the present invention is used in the following manner. During an eye examination or during surgery, the rounded surface 30 or 32 or 130 or 132 is positioned adjacent the sclera at the desired position. The blade 28 or 128 is then moved in either the first or second direction out of the plane defined by the handle 12 or 112 and the extension member 24 or 124 so that the rounded surface depresses the sclera. This can be done by either moving the handle 12 or 112 sideways to the left or right or by rotating the handle about its axis.

In addition to the foregoing, the embodiment of the invention shown in FIGS. 1 and 2 with the bulbous blade 28 there are additional advantages over the prior art. Because of the bulbous shape, it can be moved in almost any direction for the purpose of scleral depression. The most likely directions would be in a circle perpendicular to the axis of the extension. So, if an assistant is depressing the nasal side of the eye, the motion of the blade would be in the general direction of the assistant. In all cases, however, there would be minimal interference with the surgeon or any surgical instruments.

The present invention may be embodied in other specific forms without departing from the spirit or essential attributes thereof and accordingly, reference should be made to the appended claims rather than to the foregoing specification as indicating the scope of the invention.

I claim:
1. A scleral depressor comprising:
   an elongated handle having a distal end and a proximal end and defining a first axis;
   an extension member having a first end attached to the proximal end of said handle and having a second remote end, said extension member defining a second axis extending at an angle between approximately 90° to 120° from said first axis; said first and second axes defining a plane, and
   a blade carried by said extension member at the remote end thereof, said blade including a first rounded surface extending out of said plane in a first direction approximately 90° from said plane and a second rounded surface extending out of said plane in a second direction substantially opposite to said first direction and wherein said blade is bulbous shaped extending in all directions about said second axis and is wider than said extension member.

2. The scleral depressor as claimed in claim 1 wherein the angle between said first and second axes is approximately 90°.

3. A scleral depressor comprising:
   an elongated handle having a distal end and a proximal end and defining a first axis;
   an extension member having a first end attached to the proximal end of said handle and having a second remote end, said extension member defining a second axis extending at an angle between approximately 90° to 120° from said first axis; said first and second axes defining a plane, and
   a blade carried by said extension member at the remote end thereof, said blade including a first rounded surface extending out of said plane in a first direction approximately 90° from said plane and a second rounded surface extending out of said plane in a second direction substantially opposite to said first direction, said blade being substantially cylindrically shaped and wherein the diameter of said cylindrically shaped blade is greater than the width of said extension member.

4. The scleral depressor as claimed in claim 3 wherein the angle between said first and second axes is approximately 90°.

* * * * *